(12) United States Patent
Thayumanavan et al.

(10) Patent No.: US 8,969,026 B2
(45) Date of Patent: Mar. 3, 2015

(54) POLYMERIC REVERSE MICELLES AS SELECTIVE EXTRACTION AGENTS AND RELATED METHODS OF MALDI-MS ANALYSIS

(75) Inventors: Sankaran Thayumanavan, Amherst, MA (US); Richard Vachet, Belchertown, MA (US); Elamprakash N. Savariar, San Diego, CA (US); Marianny Y. Combariza, Predecuesta (CO)

(73) Assignee: University of Massachusetts, Boston, MA (US)

( * ) Notice: Subject to any disclaimer, the term of this patent is extended or adjusted under 35 U.S.C. 154(b) by 1397 days.

(21) Appl. No.: 12/672,976

(22) PCT Filed: Aug. 11, 2008

(86) PCT No.: PCT/US2008/009575
§ 371 (c)(1),
(2), (4) Date: Apr. 6, 2012

(87) PCT Pub. No.: WO2009/023158
PCT Pub. Date: Feb. 19, 2009

(65) Prior Publication Data
US 2012/0183983 A1 Jul. 19, 2012

Related U.S. Application Data

(60) Provisional application No. 60/964,230, filed on Aug. 10, 2007.

(51) Int. Cl.
 C12Q 1/37 (2006.01)
 G01N 33/00 (2006.01)
 G01N 1/18 (2006.01)
 G01N 33/68 (2006.01)
 C07K 1/14 (2006.01)
(52) U.S. Cl.
 CPC ............ *G01N 33/6851* (2013.01); *C07K 1/145* (2013.01)

USPC ................................. 435/23; 436/86; 436/178
(58) Field of Classification Search
None
See application file for complete search history.

(56) References Cited

U.S. PATENT DOCUMENTS

2006/0214104 A1  9/2006  Pope et al.
2007/0018478 A1  1/2007  Martin et al.

FOREIGN PATENT DOCUMENTS

WO  2006093525  9/2006

OTHER PUBLICATIONS

Trauger et al. Peptide and protein analysis with mass spectrometry. Spectroscopy, 2002. vol. 16, pp. 15-28.*
Hilhorst et al. Protein extraction using reversed micelles. Pure and Applied Chemistry, 1992. vol. 64, Nol. 11, pp. 1765-1770.*
Basu, S; Vutnkuri, DR; Thayumanavan, S. Homopolymer Micelles in Heterogeneous Solvent Mixtures. J. Am. Chem. Soc. 2005, 127, pp. 16794-16795.
Rodthongkum, N; Washington, JD; Savariar, E; Thayumanavan, S; Vachet, RW. Generating Peptide Titration-Type Curves Using Polymeric Reverse Micelles as Selective Extraction Agents along with Matrix-Assisted Laser Desorption Ionization-Mass Spectrometry Detection. Anal. Chem. vol. 81, No. 12, Jun. 15, 2009, pp. 5046-5053.
Rodthongkum, N; Chen, Y; Thayumanavan, S; Vachet, RW. Matrix-Assisted Laser Desorption Ionization—Mass Spectrometry Signal Enhancement of Peptides after Selective Extraction with Polymeric Reverse Micelles. Anal. Chem. vol. 82, No. 9, May 1, 2010, pp. 3686-3691.
Gomez-Escudero, A; Azagarsamy, A; Theddu, N; Vachet, RW; Thayumanavan, S. Selective Peptide Binding Using Facially Amphiphilic Dendrimers. J. Am. Chem. Soc., vol. 130, No. 33, 2008, pp. 11156-11163.

* cited by examiner

*Primary Examiner* — Marcela M Cordero Garcia
(74) *Attorney, Agent, or Firm* — Cantor Colburn LLP

(57) ABSTRACT

Methods for liquid-liquid extraction, as can be effected using polymeric reverse micelles, such methods as can be used in conjunction with various mass spectrometric techniques.

20 Claims, 14 Drawing Sheets

US 8,969,026 B2

POLYMERIC REVERSE MICELLES AS SELECTIVE EXTRACTION AGENTS AND RELATED METHODS OF MALDI-MS ANALYSIS

This application claims priority benefit of application Ser. No. 60/964,230 filed Aug. 10, 2007, the entirety of which is incorporated herein by reference.

The United States government has certain rights to this invention pursuant to Grant No. N000140510501 from the Office of Naval Research to the University of Massachusetts.

BACKGROUND OF THE INVENTION

Matrix-assisted laser desorption/ionization (MALDI) mass spectrometry (MS) is an effective method for analyzing peptides and proteins and therefore has a significant role in proteomics. When samples are complex (e.g. multi-protein digests, cell lysates, tissue extracts, etc.) or when the analyte(s) of interest are in very dilute solutions, MALDI-MS analyses can be difficult. Consequently, sample cleanup methods that eliminate interferences while simultaneously providing selective extraction of the desired analytes are valuable. Numerous on-probe clean-up methods for MALDI have been developed, but most are limited to the elimination of salts and other interferences from the sample with little concentration of the sample. Some MALDI surfaces, however, have been developed that provide both sample clean-up and concentration. Alternate approaches to on-probe clean-up methods are sample preparation protocols that simultaneously purify and concentrate peptides before depositing them on the MALDI probe. These methods rely mostly on traditional chromatographic techniques or solid-liquid extractions that are driven by a variety of interactions between the analyte and the solid support. These approaches decouple the extraction and MALDI analysis steps so that both can be independently optimized.

Liquid-liquid extractions using two immiscible phases are another means by which analyte purification and concentration can be performed. Such liquid-liquid extractions are advantageous in that they provide analyte extraction, purification, and concentration in a single step. Also, analyte transport rates are faster than in liquid-solid extractions, which allow reduced extraction times, and analytes can be quickly and easily concentrated via evaporation of organic solvents. Typically, however, these liquid-liquid extractions are limited to hydrophobic analytes and have very limited potential in peptide and protein analyses unless the organic phase can be modified in some way. Accordingly, a number of shortcomings remain in the art of preparing samples for the MALDI analysis of peptides.

SUMMARY OF THE INVENTION

In light of the foregoing, it is an object of the present invention to provide one or more systems and/or methods for peptide separation/extraction and/or mass spectral analysis, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all of its respects, to every aspect of this invention. As such, the following objects can be viewed in the alternative with respect to any one aspect of this invention.

It can be an object of the present invention to provide one or more methods for the selective separation and/or extraction of complex analyte and/or protein mixtures.

It can be another object of the present invention to provide an approach to such a separation/extraction method for in situ variation and/or tuning of a mixture medium for selective and/or sequential analyte and/or peptide separation/extraction.

It can be another object of the present invention, alone or in conjunction with one or more of the preceding objectives, to provide one or more methods relating to concentration of a separated/extracted analyte and/or peptide component or fraction to facilitate MALDI-MS analysis.

It can be another object of the present invention to likewise provide a method of enhancing analyte and/or peptide ion signals and/or yields, with enhanced signal/noise ratios, to facilitate mass spectrometric analysis at analyte and/or peptide concentrations otherwise not possible.

Other objects, features, benefits and advantages of the present invention will be apparent from this summary and the following descriptions of certain embodiments, and will be readily apparent to those skilled in the art having knowledge of various peptide and/or mass spectral analysis techniques. Such objects, features, benefits and advantages will be apparent from the above as taken into conjunction with the accompanying examples, data, figures and all reasonable inferences to be drawn therefrom, alone or with consideration of the references incorporated herein.

In part, the present invention can be directed to a method of using an amphiphilic polymeric reverse micelle for selective analyte extraction. Whether or not used in conjunction with MALDI-MS analysis, such a method can comprise providing an aqueous medium comprising a plurality of analyte components, with such a medium comprising a pH lower or higher than the isoelectric point (pI) of at least one analyte component therein; and contacting or mixing the aqueous medium and another medium at least partially immiscible with the aqueous medium, with the other medium comprising an amphiphilic polymeric compound at a concentration at least partially sufficient for reverse micelle assembly therein and comprising at least one moiety capable of interactive affinity for or association (e.g., without limitation, a chemical attraction, electrostatic interaction and/or physical compatibility) with an analyte component at an isoelectric point above or below the pH of the aqueous medium. In certain non-limiting embodiments, one or more such analytes can be a peptide component.

Regardless, in certain embodiments, such a method can be used in conjunction with a polymeric compound of a formula

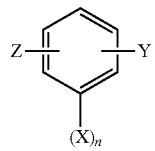

wherein X can be selected from alkylene and substituted alkylene moieties, and n denotes a numeric plurality thereof; and Y and Z can independently comprise and can be independently selected from alkylcarboxylic acid (—RCO$_2$H), substituted alkylcarboxylic acid, alkylcarboxylic acid salt, substituted alkylcarboxylic acid salt, alkylcarboxylic acid ester, substituted alkylcarboxylic acid ester, alkylcarboxamide, substituted alkylcarboxamide, alkylamidoalkylimidazole, substituted alkylamidoalkylimidazole, alkylamidoalkylimidazolium salt, substituted alkylamidoalkylimidazolium salt, alkylimidazole, substituted alkylimidazole, alkylimidazolium salt, substituted alkylimidazolium salt and corresponding heteroatom-substituted (e.g., oxa, aza, etc.) moieties (e.g., without limitation, oxyacetic acid, substituted oxyacetic acid, oxyacetic acid salt, substituted oxyacetic acid salt, oxyacetic acid ester, oxyacetamide, and substituted oxyacetamide, oxyalkylimidazole, oxyalkylimidazolium salt, oxyalkylamidoalkylimidazole, oxyalkylamidoalkylimidazolium salt, and substituted variations of such moieties), poly(ethylene oxide), substituted poly(ethylene oxide), benzoxy, substituted benzoxy, alkoxy and substituted alkoxy moieties, with Y and Z moieties selected to provide amphiphilic character to the polymer, regardless of position (e.g., meta) with respect to X and a micellar configuration and/or assembly upon contact with a fluid medium.

Such X, Y and Z components would be well known to those skilled in the art made aware of this invention. For instance, component Y can comprise a carboxylic acid/carboxylate moiety (e.g., acetic acid/acetate). In certain embodiments, such as those described herein, component Y can be an oxyacetic acid substituent. Likewise, component Z can comprise an alkylphenyl moiety (e.g., benzyl). In certain embodiments, such as those described herein, component Z can be a benzoxy substituent. Further, component X can be derived from an unsaturated moiety, limited only by an ability to undergo polymerization without adversely affecting the chemical or structural integrity of components Y and Z.

As illustrated herein, such a compound can be homopolymeric, but can also incorporate various other monomers or components, such incorporation limited only so as to not unduly compromise polymeric configuration and/or micellar assembly of the type described herein. Likewise, such polymers are not limited to monomers having a meta relationship; that is, Y or Z can be ortho or para with respect to X.

In certain embodiments, such a Y or Z moiety can comprise an acid group and/or its conjugate base. In certain such embodiments, such a group can comprise a carboxylic acid and/or the corresponding carboxylate. Such polymeric compounds, moieties and/or groups thereof are limited only by interactive affinity and/or electrostatic interaction with one or more peptide components having an isoelectric point above the pH of the aqueous medium. In certain other embodiments, such a Y or Z moiety can comprise a basic group and/or its conjugate acid. In certain such embodiments, such a moiety can comprise an imidazole and/or the corresponding imidazolium group. Such polymeric compounds, moieties and/or groups thereof are limited only by interactive affinity and/or electrostatic interaction with one or more peptide components having an isoelectric point below the pH of the aqueous medium. Such and various other polymeric compounds, moieties, groups and/or micellar assemblies thereof, of the sort useful in conjunction with this invention, are discussed more fully in co-pending application Ser. No. 11/184,342, filed Jul. 19, 2005, the entirety of which is incorporated herein by reference.

Regardless, in certain embodiments, the pH of the aqueous medium can be adjusted to a value lower or higher than the isoelectric point of other analyte components within the aqueous medium, depending on the polymeric compounds, moieties, and/or groups thereof used in conjunction therewith. Accordingly, in certain embodiments, a plurality of peptide components can be selectively extracted, in sequence, with corresponding pH adjustment. Alternatively, from another perspective, such peptide component(s) can be extracted and/or concentrated for further analysis. With regard to one such embodiment, each selectively-extracted peptide component(s) can be applied to a target component of a mass spectrometer. A mass spectrum of the extracted peptide component(s) can be acquired, as described below and/or as would be understood by those skilled in the art of mass spectrometric analysis.

In part, the present invention can also be directed to a method of sequential fractionization of a peptide mixture. Such a method can comprise providing an aqueous medium comprising a plurality of peptide fractions, such a medium comprising a pH below or higher than the isoelectric point of at least one peptide fraction of the mixture; contacting the aqueous medium and another medium at least partially immiscible with the aqueous medium, the other medium comprising an amphiphilic polymeric compound of the sort described herein, to separate a peptide fraction by isoelectric point; adjusting the pH of the aqueous medium below or higher than the isoelectric point of another peptide fraction of the mixture; and contacting the aqueous medium and another medium at least partially immiscible with the aqueous medium, the other medium comprising an amphiphilic polymeric compound, to separate another corresponding peptide fraction by isoelectric point. Accordingly, iterative pH adjustments and polymeric compound contacts can be used to sequentially separate peptide fractions from the mixture.

Without limitation, the peptide mixture used in conjunction with such a method can be selected from multi-protein digests, cell lysates and tissue extracts. Regardless, each sequentially separated fraction can be analyzed by mass spectrometry as described elsewhere herein and/or by one or more other detection techniques including but not limited to fluorescence spectroscopy and UV-VIS spectroscopy. As would be understood by those skilled in the art and as illustrated elsewhere herein, the isoelectric point of each separated fraction and the corresponding m/z ratios obtained through the mass spectral analysis can be used to identify the peptide source of each fraction and/or component thereof.

In part, the present invention can also be directed to a method for MALDI-MS spectrometric analysis of an analyte and/or peptide mixture. Such a method can comprise providing an aqueous medium comprising a plurality of analyte/peptide components or fragments, such a medium comprising a pH lower or higher than the isoelectric point of at least one analyte/peptide component or fragment; contacting the aqueous medium and another medium at least partially immiscible therewith, the immiscible medium comprising an amphiphilic polymeric compound of the sort described herein; applying the extracted analyte/peptide component(s)/fragment(s) to a mass spectrometer target; and acquiring the MALDI-MS spectrum of the extracted analyte/peptide component(s)/fragment(s), such a spectrum comprising analyte/peptide ion signals for each extracted analyte/peptide component. Without limitation, indicative of a utility of such a method, a MALDI-MS spectrum of the aforementioned aqueous medium can be absent such analyte/peptide ion signals prior to extraction. In certain such embodiments, such a analyte/peptide mixture can have a concentration less than about 5 nM, and a MALDI-MS spectrum of such a medium can be absent observable and/or reproducible analyte/peptide ion signals. After implementation of such a method, analyte/peptide ion signals corresponding to the extracted analyte/peptide component(s)/fragment(s) can be observable at peptide concentrations less than about 5 nM. In certain embodiments, as demonstrated below, observable analyte/peptide ion signals can be acquired at analyte/peptide concentrations down to about 10 pM or less.

Accordingly, this invention can also be directed to a method of using an amphiphilic polymeric micelle to enhance the MALDI-mass spectrometric signal of a peptide component. Such a method can comprise providing an aqueous medium comprising a plurality of peptide components, such components at a concentration less than sufficient to provide a MALDI signal under mass spectrometric conditions; adjusting the pH of the aqueous medium below or higher than the isoelectric point of at least one peptide component within the aqueous medium; contacting the aqueous medium and another medium at least partially immiscible therewith and comprising an amphiphilic polymeric compound at a concentration at least partially sufficient for micelle assembly, such a polymeric compound of the sort described herein, and such contact at least partially sufficient to extract peptide component(s) according to their isoelectric point(s); and acquiring the MALDI-MS spectrum of the extracted peptide component(s). The resulting spectrum can comprise peptide ion signals for each said extracted peptide component, such signals absent before extraction. Without limitation, in certain embodiments of such a method, the mass spectrum of each extracted peptide component can be observable at a concentration less than about 5 nM. In certain such embodiments, observable peptide ion signals can be acquired at peptide concentrations down to about 10 pM or less.

Separation and analyses of peptides in complex mixtures are significant challenges in proteomics applications and represent but a few of the end use applications available through use of this invention. As demonstrated below by several non-limiting embodiments, an amphiphilic polymer-based nanoassembly of this invention is capable of selectively extracting peptides, based on their isoelectric points, into an immiscible organic phase from an aqueous solution. The isoelectric point cut-off in these extractions can depend on the pH of the aqueous solution, and thus sequential fractionation of peptide mixtures based on pI can be accomplished by varying the pH of the aqueous solution. Additionally, an unexpected enhancement in the MALDI-MS signal can be observed for extracted peptides ionized in the presence of such a polymer, which in turn can provide reproducible ion signals for some peptides at concentrations as low as 10 pM.

DETAILED DESCRIPTION OF CERTAIN EMBODIMENTS

As shown by several embodiments, this invention can employ polymers comprising amphiphilic monomeric units to selectively extract peptides into an organic phase, optionally for subsequent analysis by MS. A class of amphiphilic polymers, such as 1, below (together with various other alkylether substituted polymers), are capable of forming micelle-type assemblies in water and inverse micelle-type assemblies in apolar solvents. These nanostructures are kinetically trapped in the solvent that they are initially assembled in; they do not thermodynamically distribute themselves in an immiscible mixture of polar and apolar solvents. This feature provides a unique opportunity to use the inverse micelle-type assemblies as part of a liquid-liquid extraction protocol. Consistent with such results these inverse micelles can selectively extract peptides based on electrostatic interactions. For instance, inverse micelles formed from 1 can selectively extract and concentrate peptides from very dilute solutions, which otherwise do not provide any MALDI signal. In addition, the presence of these polymeric materials leads to significant enhancements in ion yields during the MALDI process, highlighting further advantages of the current method of peptide extraction and detection. The general approach afforded by this invention is versatile, the selectivity of extraction is tunable in situ, and the detection sensitivity is high.

The net charge within the inverse micelle of 1 is negative, affording a selective extraction of positively-charged peptides. In a typical experiment, a toluene solution containing 1 was mixed with an aqueous solution containing a mixture of peptides. After vortexing this mixture, the organic layer was separated and analyzed using MALDI-MS. FIG. 1A shows a MALDI mass spectrum for a mixture of peptides before extraction, and FIGS. 1B and 1C show MALDI mass spectra obtained for the organic and aqueous phases, respectively, after extraction with the inverse micelles. Because the aqueous solution was buffered at a pH of 7.1, peptides with pI values above 7.1 were expected to be sequestered into the interior of the inverse micelles, while peptides with pI values below 7.1 would be mostly excluded based on Coulombic repulsion. Indeed, results show that peptides with pI values above 7.1 are effectively extracted and concentrated, while peptides with pI values below 7.1 are generally not.

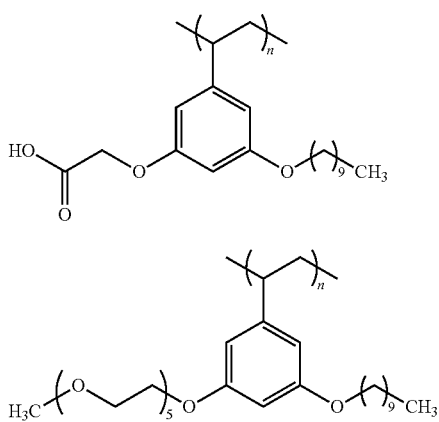

Figure 2:
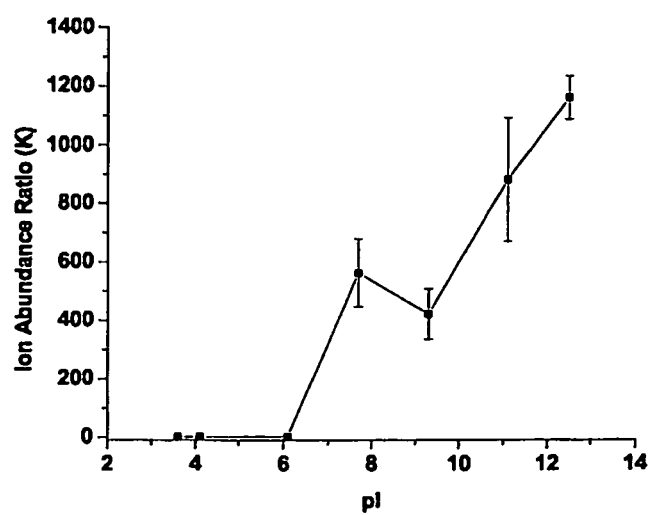
FIG. 2. Plot of ion abundance ratio vs. pI for the peptides shown in Table 1 after an extraction at pH 7.1. The error bars represent the standard error of the mean from 5 replicate measurements.

FIG. 2 clearly shows this trend for several peptides by plotting the ion abundance ratio (K) as a function of the peptide pI. The ion abundance ratio is related to the extraction capacity of the polymer, and can be defined as the ratio of the MALDI ion abundance of the peptide in the organic phase that contains the inverse micelles ($I_{org}$) to the ion abundance of the peptide remaining in the aqueous phase ($I_{aq}$) ($K = I_{org}/I_{aq}$). These experiments were performed with the hypothesis that the extraction would be based on electrostatic interaction between the polymer and the peptide. To test this premise further, two control experiments were carried out. First, it is necessary to identify that the calculated ion abundance ratios do not represent the inherent distribution coefficient for the peptides in water vs. toluene. Therefore, a two-phase extraction experiment was done in the absence of homopolymer 1, and no peptide extraction into the organic phase was observed. Second, peptide extractions using a polymer without the negatively-charged functionality were performed. Polymer 2 contains charge-neutral pentaethyleneglycol functionalities instead of the carboxylic acid moieties. This polymer also forms inverse micelles in apolar solvents; however, when the peptide extraction experiment was carried out with polymer 2, no discernible extraction was observed (data not shown). These two results are consistent with the hypothesis that the extraction is based on electrostatics.

Considering these results, it was ascertained that the cut-off pI can be tuned by simply modifying the pH of the aqueous solution. Without limitation to any one theory or mode of operation, the pH of the overall aqueous solution is also likely to dictate the pH of the hydrated interiors of the inverse micelle where the binding takes place. Accordingly, extractions at three different pHs: 4.0, 7.1, and 9.0 were carried out; the results of these experiments are listed in Table 1. It is clear that when the experiments were carried out at pH 4.0 the preproenkephalin peptide with a pI of 3.6 was not efficiently extracted, whereas all the other peptides were extracted into the organic layer. This result shows that the extraction cut-off can be tuned. The results from experiments at pH 7.1 and 9.0 further support this idea. It should be noted that when the experiment is carried out at pH 9.0, the peptide with a pI of 7.7 is extracted to some extent. Such a result could be attributed to errors associated with aqueous solution pH measuring or to errors in the peptide pI calculation. Nonetheless, the tunability is still significant and therefore is a very useful result.

TABLE 1 pH-dependent ion abundance ratios of various peptides

Figure 1:
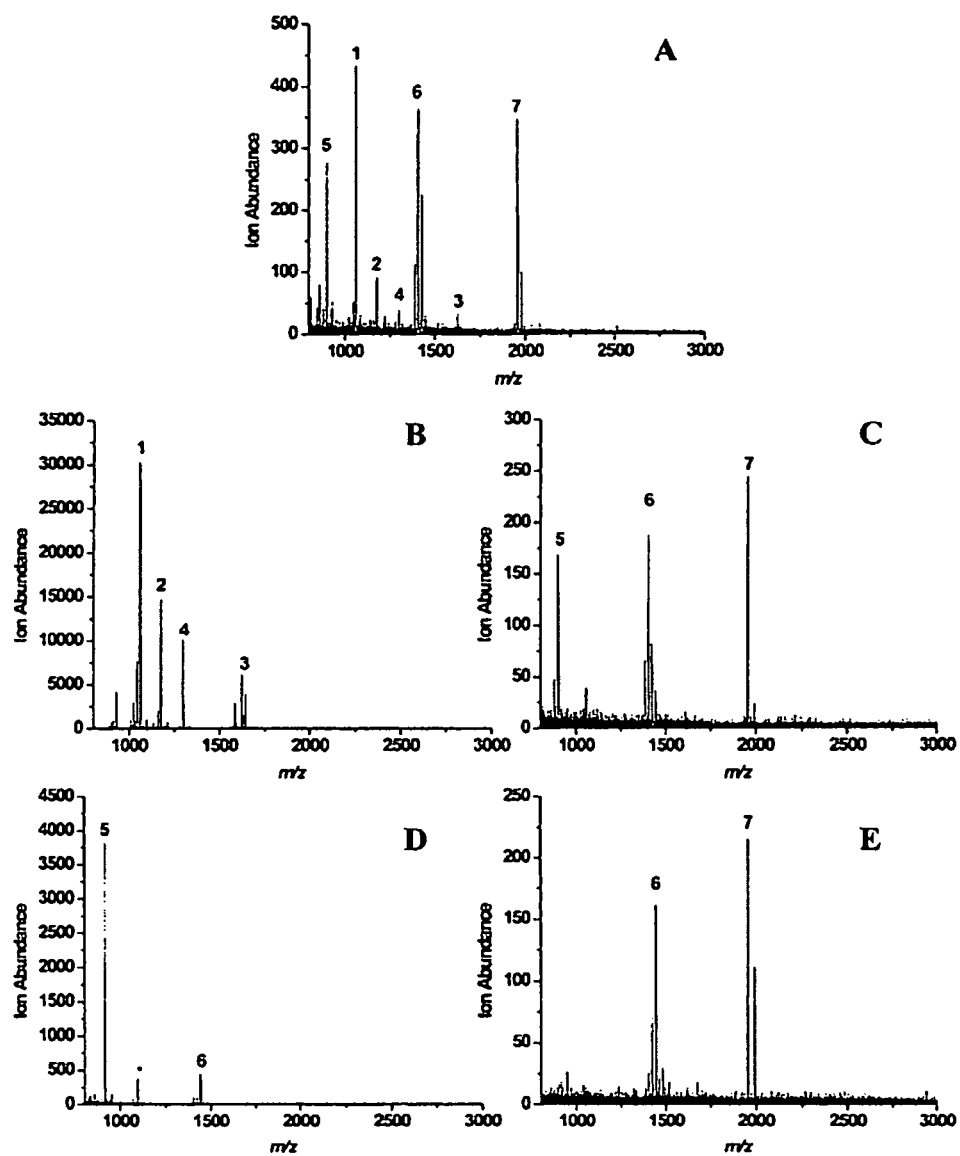
FIGS. 1A-E. A) MALDI mass spectrum of the peptide mixture in the initial aqueous solution; B) MALDI mass spectrum of the organic extract after an extraction procedure using polymer 1 at pH=7.1; (C) MALDI mass spectrum of the aqueous solution remaining after the extraction procedure using polymer 1 at pH=7.1; (D) MALDI mass spectrum of the organic extract after an extraction procedure using polymer 1 at pH=7.1 followed by an extraction at pH 5.5; (E) MALDI mass spectrum of the aqueous phase after an extraction procedure using polymer 1 at pH=7.1 followed by the extraction at pH 5.5. Peaks marked with an asterisk (*) are ions associated with the polymer or the matrix. See Table 1 for peptide labels.

| Peak in FIG. 1 | Peptide (pI)[a] | Ion abundance ratio (K ± $s_M$)[b] | | |
|---|---|---|---|---|
| | | pH 4.0 | pH 7.1 | pH 9.0 |
| 1 | Bradykinin (12.5) | 680 ± 138 | 1162 ± 73 | 842 ± 151 |
| 2 | Kinetensin (11.1) | 337 ± 79 | 882 ± 212 | 616 ± 198 |
| 3 | ACTH Human (9.3) | 221 ± 37 | 422 ± 87 | 128 ± 41 |
| 4 | Angiotensin I (7.7) | 237 ± 56 | 563 ± 116 | 34 ± 14 |
| 5 | Spinorphin (6.1) | 36 ± 12 | 2.0 ± 1.0 | 1.0 ± 0.5 |
| 6 | β-Amyloid (4.1) | 17 ± 6 | 0.4 ± 0.2 | 0.10 ± 0.07 |
| 7 | Preproenkephalin (3.6) | 2.2 ± 0.9 | 0.4 ± 0.1 | 0.12 ± 0.04 |

[a]Calculated using the program available at http://bioweb.pasteur.fr/docs/EMBOSS/pepstats.html.
[b]The ion abundance ratio is defined as the ratio of the MALDI ion abundance of the peptide in the organic phase that contains the inverse micelles ($I_{org}$) to the ion abundance of the peptide remaining in the aqueous phase ($I_{aq}$) ($K = I_{org}/I_{aq}$). Ion abundance ratio values (K) and standard errors of the mean ($s_M$) were for the $[M+H]^+$ signal, except for spinorphin and β-amyloid where values were calculated using the $[M+K]^+$ signal. In each case, the $s_M$ values are from at least 4 replicate measurements.

The utility of a pH-tunable extraction procedure, of this invention, is further illustrated through a sequential extraction protocol to separate out a small number of peptides from a sample containing a mixture of peptides. For this purpose two consecutive extractions at pH 7.1 and 5.5 were done using a mixture of peptides shown in Table 1 and following the protocol described in the experimental section. FIG. 1A shows the MALDI mass spectrum of the mixture of the seven peptides in aqueous solution. FIG. 1B shows the results of the first extraction, when the pH of the aqueous solution was 7.1. FIG. 1C shows the aqueous phase after the first extraction. These data show that all of the peptides except β-amyloid, spinorphin, and preproenkephalin are extracted into the organic layer upon a pH 7.1 extraction. FIG. 1D shows the organic phase after the second extraction, when the pH of the aqueous solution remaining after the first extraction is lowered to 5.5. At this point, spinorphin is extracted into the organic layer. In addition, FIG. 1D shows that a small amount of β-amyloid was extracted when the pH of the aqueous solution was adjusted to 5.5. This result indicates that a small fraction of this peptide could be positively charged at pH 5.5 and therefore extracted into the organic phase. The remaining aqueous solution after the second extraction contains only β-amyloid and preproenkephalin (FIG. 1E), which is expected based on the pIs of these peptides. Overall, these results show that a pH-dependent tunability of the extraction cut-off can be effectively used to further clean-up samples for analyses. Furthermore, the sensitivity of this approach is quite evident as single peptides (e.g. spinorphin) can be detected after extraction at the appropriate pH.

To further validate a utility of this invention, the performance of amphiphilic homopolymer 3, as another representative embodiment of these materials, was evaluated on a series of pI markers that are commonly used as references in isoelectric focusing because of their well-defined pI values.

3

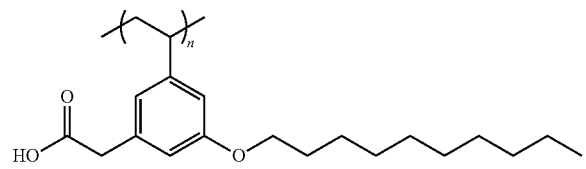

Fluorescent pI markers were chosen so that fluorescence spectroscopy could be used to sensitively detect and quantitatively assess the extent of extraction. While application of an embodiment of this invention can be to extract and concentrate peptides for analysis by MALDI-TOF-MS, the relative quantitative ability of MALDI-MS can make fluorescence spectroscopy, in some instances, a better choice for accurately and quantitatively assessing the use and application of the polymeric reverse micelles of this invention. The data, discussed below, demonstrate that an analyte's $pK_a$ values and aqueous solution pH are among factors controlling the extraction selectivity of the polymeric reverse micelles. The extent of extraction follows very closely that predicted based upon the known $pK_a$ values, demonstrating that these materials can be used to generate analyte titration curves. The chemical names, structures, pI and $pK_a$ values of 9 representative markers are shown in Table 2.

TABLE 2

Chemical names, structures, pI and $pK_a$ values of the 9 markers used in this study. (See, M. Horká, T. Willimann, M. Blum, P. Nording, Z. Friedl and K. Šlais, *J. Chrom. A*, 2001, 916, 65-71.)

| No. | Structures | pI | $Pk_{a1}$ | $Pk_a$ |
|---|---|---|---|---|
| 1 | 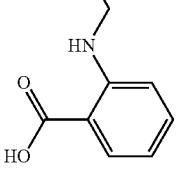  2-[(carboxymethyl)amino]benzoic acid | 2.1 | 1.50 | 2.70 |
| 2 | 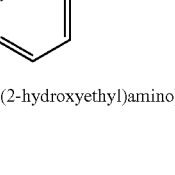  5-chloro-2-[(2-hydroxyethyl)amino]benzoic acid | 3.0 | 1.69 | 4.35 |
| 3 | 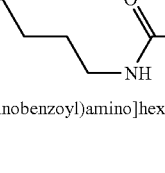  6-[(2-aminobenzoyl)amino]hexanoic acid | 4.0 | 3.20 | 4.80 |
| 4 | 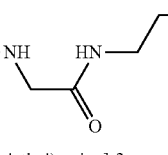  2-({2-[(2-morpholin-4-ylethyl)amino]-2-oxoethyl}amino)benzoic acid | 5.1 | 3.94 | 6.30 |

TABLE 2-continued

Chemical names, structures, pI and pK$_a$ values of the 9 markers used in this study. (See, M. Horká, T. Willimann, M. Blum, P. Nording, Z. Friedl and K. Šlais, *J. Chrom. A*, 2001, 916, 65-71.)

| No. | Structures | pI | Pk$_{a1}$ | Pk$_a$ |
|---|---|---|---|---|
| 5 | 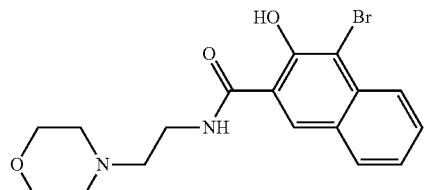<br>4-bromo-3-hydroxy-N-(2-morpholin-4-ylethyl)-2-naphthamide | 6.2 | 5.35 | 6.95 |
| 6 | 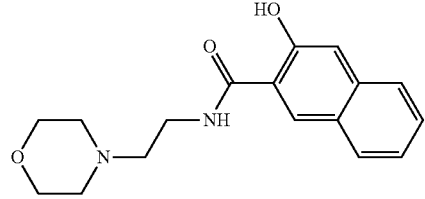<br>3-hydroxy-N-(2-morpholin-4-ylethyl)-2-naphthamide | 7.2 | 6.20 | 8.10 |
| 7 | 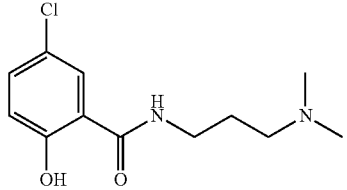<br>5-chloro-N-[3-(dimethylamino)propyl]-2-hydroxybenzamide | 8.1 | 6.80 | 9.30 |
| 8 | 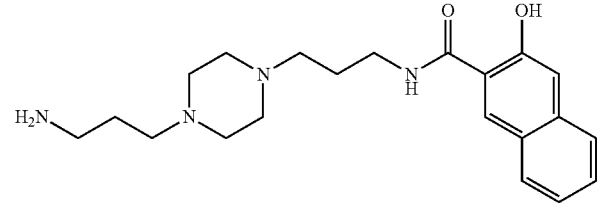<br>N-{[4-(aminopropyl)piperazin-1-yl]propyl}-3-hydroxy-2-naphthamide | 9.0 | 8.05 | 9.85 |
| 9 | 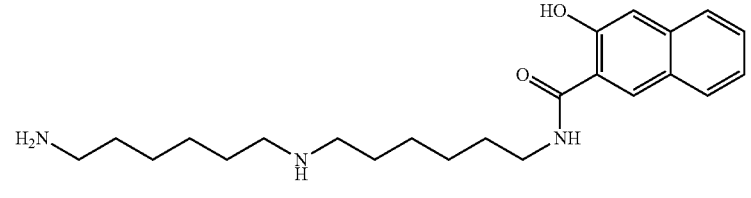<br>N-{6-[(6-aminohexyl)amino]hexyl}-3-hydroxy-2-naphthamide | 10.3 | 9.95 | 10.65 |

Figure 3:
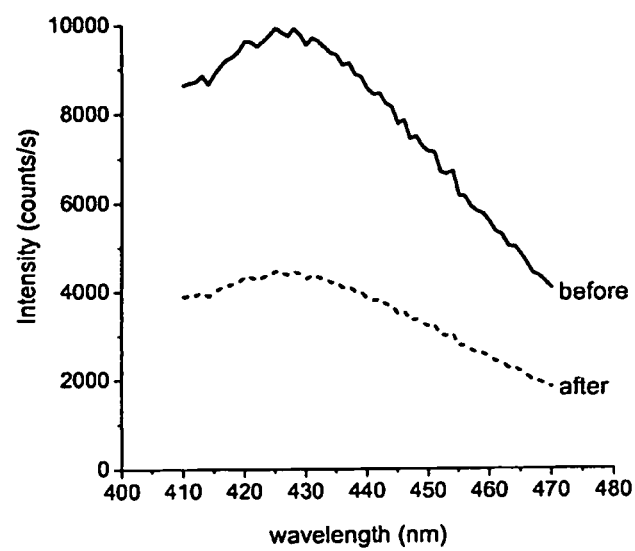
FIG. 3. Fluorescence spectra of pI marker 2 before (solid line) and after (dashed line) extraction at pH 1.9.

The polymeric reverse micelle-like nanoassemblies have carboxylate groups in their interiors; therefore, positively charged pI markers are expected to be extracted. Upon extraction, the concentrations of the pI markers left in the aqueous phase were quantitatively determined by fluorescence spectroscopy. Analysis of the organic phase was difficult because the fluorescence spectrum of the polymer is very broad in this phase, and in many cases overlaps with the signal from the pI markers. As an example of the data from the aqueous solution, the fluorescence spectra of pI marker 2, before (solid line) and after extraction (dashed line), are shown in FIG. 3. The decrease in fluorescence intensity of the pI marker in the aqueous phase after extraction indicates that most of the pI marker is extracted and transferred into the organic phase. The concentration of the pI marker remaining in the aqueous phase can be quantified, and in this example, it is determined that 46% of pI marker 2 remains, which means that 54% of it is extracted into the organic phase when the aqueous solution pH is 1.9. It is not surprising that most of this compound is extracted under these conditions. This marker hag a pI value of 3.0, and at an aqueous solution pH of 1.9, most of this compound is positively charged and therefore interacts favorably with the negatively-charged interior of the polymeric reverse micelles.

Figure 4:
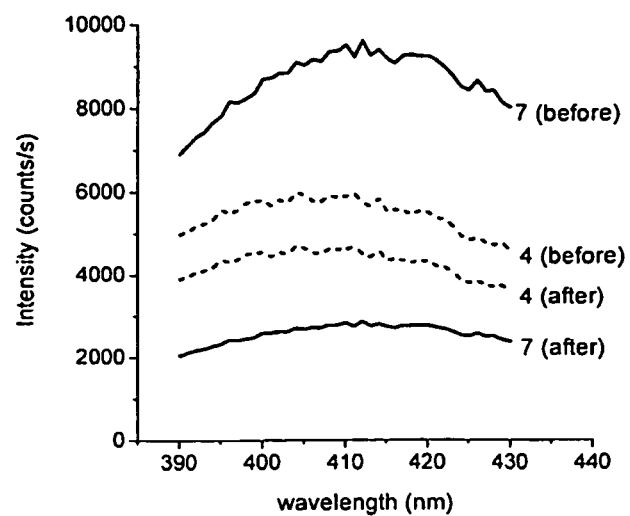
FIG. 4. Fluorescence spectra of pI marker 4 (dashed line) and pI marker 7 (solid line) before and after extraction at pH 6.0.

Previously, it was shown for a series of peptides that charge complementarity exerts an important influence on the extraction process with these amphiphilic homopolymers. (See, M. Y. Combariza, E. N. Savariar, D. R. Vutukuri, S. Thayumanavan and R. W. Vachet, Anal. Chem. 2007, 79, 7124-7130.) Here, the importance of two other factors—hydrophobicity and aqueous solution pH—are assessed. Hydrophobicity might affect the extraction efficiency to some degree due to the toluene phase that surrounds the reverse micelles and the hydrocarbon functionality on the periphery of the reverse micelles. In order to investigate this effect, extractions of pI markers with different hydrophobicities were performed. As an example of the effect of hydrophobicity, the results from the extraction of two pI markers (4 and 7) at an aqueous phase pH of 6.0 are shown in FIG. 4. Separate experiments in which pI markers 4 and 7 are extracted into toluene alone (i.e. no reverse micelles) indicate that pI marker 4 is more hydrophobic because a greater percentage of it is transferred into toluene (8.4±0.6% vs. 5.9±0.3%). Even though it is less hydrophobic, pI marker 7 (pI=8.1) is extracted more efficiently than pI marker 4 (pI=5.1) from an aqueous solution at pH of 6.0 when the reverse micelles are present in the toluene phase (FIG. 4). This greater extraction efficiency for pI marker 7 (70±1.6%) than for marker 4 (21.5±0.4%) is due to it being positively-charged at pH 6.0 whereas marker 4 is mostly negatively-charged at this pH. A comparison of the extraction efficiencies of the other pI markers indicates that there is no clear trend between extraction efficiency and analyte hydrophobicity when the reverse micelles are present in the toluene phase. Indeed, just like the data in FIG. 4, analyte charge appears to be more important.

Figure 5:
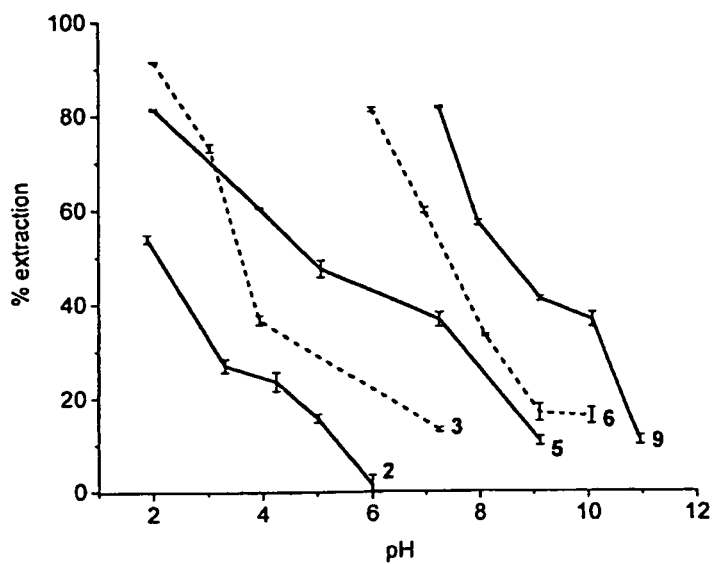
FIG. 5. Extraction percentages as a function of pH for pI markers 2 (pI=3.0), 3 (pI=4.0), 5 (pI=6.2), 6 (pI=7.2) and 9 (pI=10.3).

While aqueous solution pH will definitely control the charge of the pI markers in the aqueous phase, it is not obvious that aqueous solution pH will control the extraction process because the analyte is ultimately transferred out of the aqueous phase and into the organic phase. To test the effect of aqueous solution pH on extraction efficiency, each pI marker was extracted over a range of pH values spanning its pI value. The extraction percentages of five of the pI markers as a function of aqueous phase pH are shown in FIG. 5. Clearly, these plots demonstrate that aqueous phase pH is a critical factor controlling extraction selectivity and efficiency. All of the pI markers exhibit the same trend—they are extracted well at low pH values and poorly at high pH values. For every pI marker, the fraction of molecules that are positively charged is greatest at the lower pH values, and so the extraction efficiency is greatest. At higher pH values, a lower fraction of the molecules are positively-charged, and thus the extraction efficiency is much lower. In all cases, it can be noticed that a small percentage of each marker is still extracted at pH values well above its pI, where the negatively-charged species is dominant in solution and columbic repulsion with the reverse micelle interiors should occur. The small extraction percentage under these cases is probably due to the small percentage of positively-charged species that persists in solution and the low, albeit noticeable, affinity that each marker has for the toluene phase.

Figure 6:
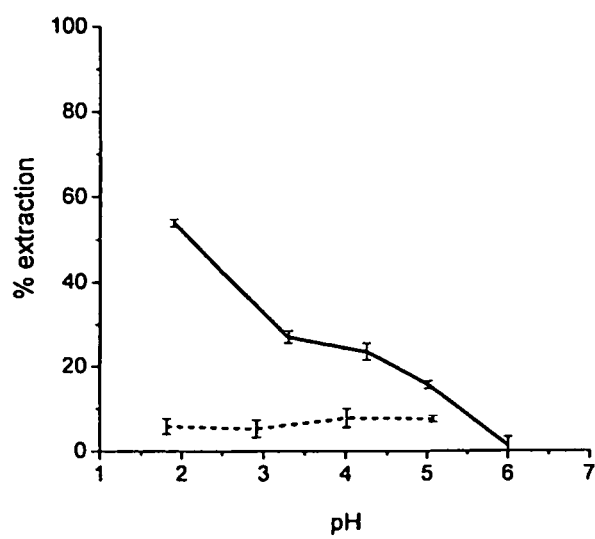
FIG. 6. Percentage extraction of pI marker 2 as a function of aqueous phase pH in the presence (solid line) and absence (dashed line) of the reverse micelles.

To test the influence of toluene on extraction efficiency, control extraction experiments were carried out in the absence of polymer at a variety of aqueous phase pHs. As an example, a plot of the extraction percentage as a function of pH for pI marker 2 shows that the pI marker has a slight affinity for toluene (FIG. 6). On average about 6.6±0.6% of pI marker 2 is extracted into the toluene phase in the absence of the polymer. Furthermore, the data show that partitioning into toluene is a pH independent process, which is somewhat surprising as toluene does not typically solvate charged species very well. Similar results are also obtained for the other markers with extraction percentages ranging from 5.5±0.8% to 8.4±0.6%. Overall, these data indicate that the small degree of extraction observed for each marker at high pH values is mostly controlled by the markers' inherent affinity for toluene.

Figure 7:
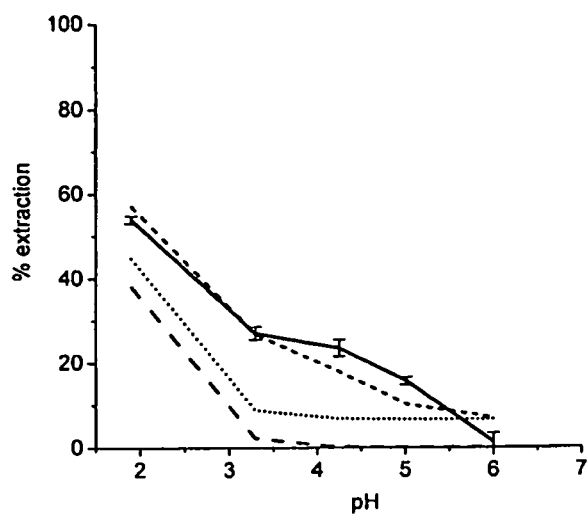
FIG. 7. A comparison of experimentally-observed and theoretically-predicted extraction percentages for pI marker 2 as a function of aqueous pH. The solid line represents the experimentally-observed data, the lowest dashed line represents the fractional composition of the positively-charged species ($MH_2^+$) calculated from the $pK_a$ values, the middle dotted line represents the sum of the calculated fractional composition of $MH_2^+$ and the percentage of the marker experimentally extracted by toluene, and the highest dashed line represents the sum of the calculated fractional composition of $MH_2^+$, the percentage of the marker experimentally extracted by toluene, and the calculated fractional composition of the neutral zwitterionic form (MH) arbitrarily multiplied by 20%.

Because the aqueous phase pH seems to control the extraction efficiency of the pI markers, the experimental data were compared with theoretical calculations of the species present in solution at the different aqueous pH values in order to better understand the extraction behavior. The $pK_a$ values of all the pI markers are known, so calculations of the fractional composition of each species are straightforward. As an example, the percentage of positively-charged species calculated for pI marker 2 is compared with the experimentally measured results (FIG. 7). If the fractional composition of only the positively-charged species (i.e. $MH_2^+$) of marker 2 is considered (FIG. 7, lowest dashed line) the general extraction trend is reproduced, but the experimental data (FIG. 7, solid line) show higher extraction percentages at all the pH values studied. This comparison indicates that simply considering the positively-charged species alone is not enough to account for the experimentally observed data. Presumably, other forms of pI marker 2 that are present in the solution could be extracted in our experiment.

To further refine the calculated values and obtain a better fit to the experimental data, two other factors were considered. First, the percentage of pI marker 2 extracted by toluene was added to the calculated fractional composition of the positively-charged species (FIG. 7, the middle dotted line). This addition results in a slightly better fit to the experimental data than considering the positively-charged species alone, but it still does not account for the entire trend, especially at pH values above 3. Second, a fraction of the neutral, in this case zwitterionic, species (i.e. MH) was added to the fractional composition of the positively-charged species and the percentage extracted by toluene alone. When 20% of neutral species is added (FIG. 7, the highest dashed line), the experimental data is fit very well at each of the pH values. This improved fit indicates that some fraction (~20%) of the neutral zwitterionic species of pI marker 2 is extracted by the reverse micelles in toluene. In this case, extraction of the zwitterionic species probably occurs because it contains a positively-charged amine group capable of interacting with the carboxylate groups in the interior of the reverse micelles. Presumably, only a fraction of the zwitterionic species is extracted because it also contains a negatively-charged group that is not as readily accommodated in either the toluene phase or the reverse micelle interiors.

Figure 8:
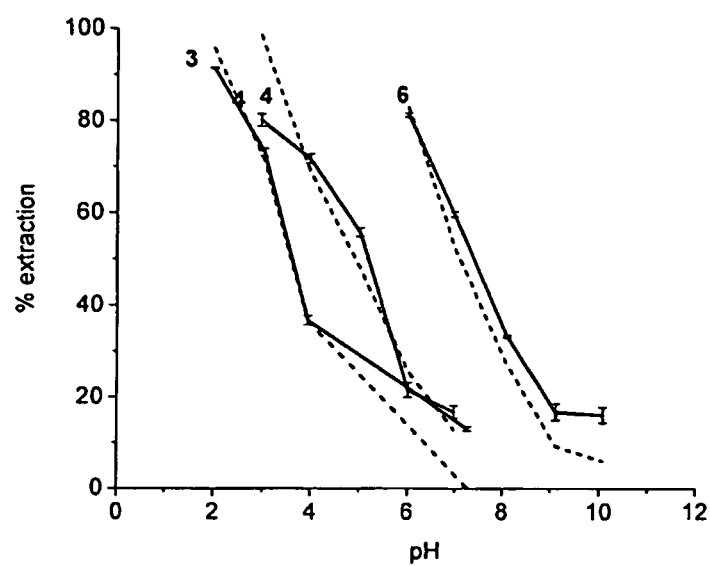
FIG. 8. A comparison of experimentally-observed (solid line) and theoretically-predicted (dashed line) extraction percentages for pI marker 3, 4, and 6 as a function of aqueous pH. In each case, the theoretical values were obtained by summing the fractional composition of the positively-charged species, the percentage of the marker experimentally extracted by toluene, and a percentage of the calculated fractional composition of the neutral form (MH). The percentage contributions of the neutral forms are 20%, 20% and 30% for markers 3, 4 and 6, respectively.
Figure 9:
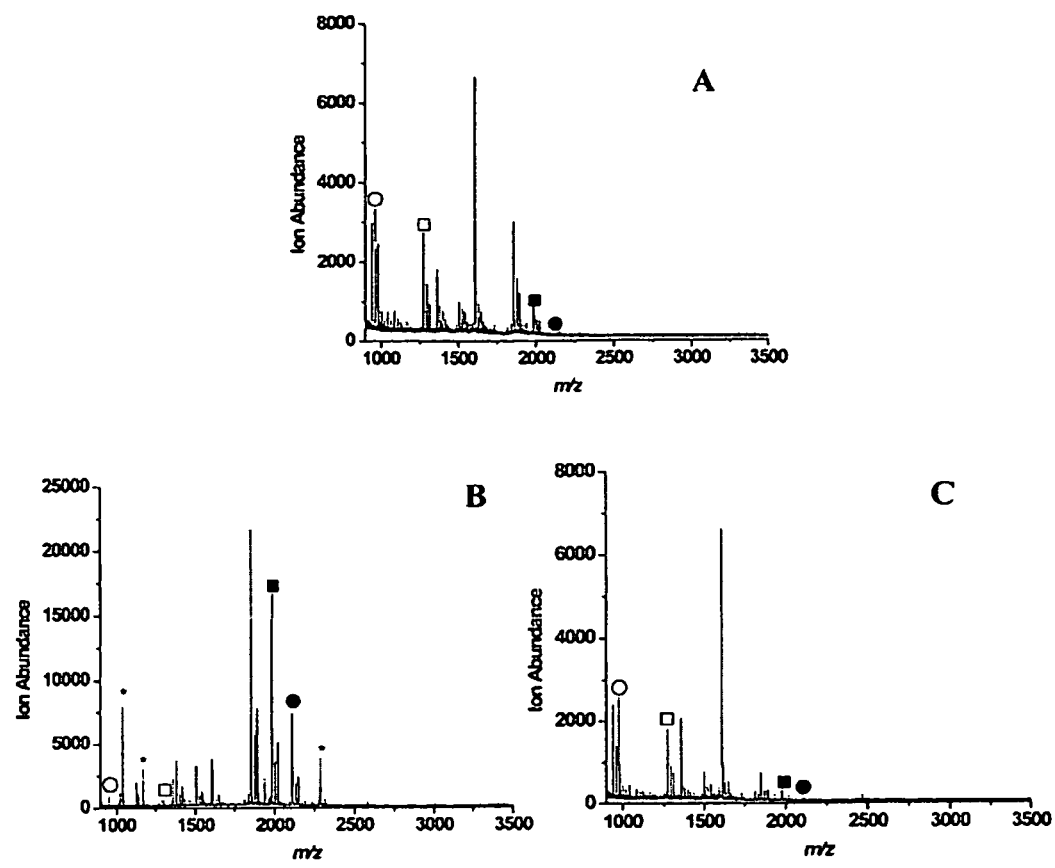
FIGS. 9A-C. A) MALDI mass spectrum of the myoglobin tryptic digest; B) MALDI mass spectrum of the organic extract after an extraction procedure using 1 at pH=7.1; (C) MALDI mass spectrum of the aqueous solution remaining after the extraction procedure using 1 at pH=7.1. Peaks marked with an asterisk (*) are ions associated with the polymer or the matrix. The open circle (○) label corresponds to the peptide YKELGFQG (SEQ ID NO: 19), the open square (□) is LFTGHPETLEK (SEQ ID NO: 3), the closed circle (●) is KKGHHEAELKPLAQSHATK (SEQ ID NO: 11), and the closed square (■) is KGHHEAELKPLAQSHA TK (SEQ ID NO: 19; see Table 2 for peptide pI, m/z, and K values).

When the same type of fitting is done for the other markers, a similar degree of agreement is achieved in each case (FIG. 8). However, the percent contribution of the neutral species is slightly different for each pI marker with an average value of 21% (Table 3). Interestingly, the best curve fittings for almost all of the pI markers are obtained when the percentage contribution of neutral species is about 20 to 30%. There is only one notable outlier, pI marker 1, which has a neutral contribution of 5%. The exact reason for this outlier is not clear, but one possibility is suggested. The close proximity of the positively-charged and negatively-charged group may not allow the negatively-charged micelle interior to interact optimally with the positively-charged group in the zwitterionic form of marker 1.

TABLE 3

The percentages contributed by the neutral species providing the best fit with theoretical calculation of the 9 pI markers.

| | pI marker | | | | | | | | |
|---|---|---|---|---|---|---|---|---|---|
| | 1 | 2 | 3 | 4 | 5 | 6 | 7 | 8 | 9 |
| % neutral contribution | 5 | 20 | 20 | 20 | 30 | 30 | 30 | 20 | 20 |

Such results demonstrate the extraction behavior of the amphiphilic homopolymer reverse micelles. Specifically, the data indicates the following: (i) an analyte's charge state in aqueous solution, which is controlled by its $pK_a$ values and the aqueous phase pH, a contributor to extraction selectivity and efficiency; (ii) analyte hydrophobicity plays a relatively unimportant role; (iii) neutral compounds can be extracted, but the percentage of neutral species extracted is around 20-30% for all but one of the compounds examined. When considering contributions from neutral species, a good correlation between experiment and theory can be made, suggesting that the reverse micelles can be useful for generating "titration curves" for analytes. Such curves, along with mass spectrometric detection, might allow this protocol to be used in proteomic analyses. Peptide titration curves may be predictable, and such data might be beneficial as a database search constraint in protein identification experiments.

Another potential application of this inverse micellar extraction procedure is the selective fractionation of peptides from protein digests. As demonstrated, upon choosing the pH of the aqueous solution, only peptides with pI values above that pH would be extracted and detected. It would then be known that the extracted and detected peptides have a limited range of pI values, and this coupled with the m/z of these peptide ions might be used to help identify the protein from which the fragments arise. Recent work suggests that accurate peptide m/z ratios along with peptide pI values can reduce the number of false positives associated with protein identification in peptide mass fingerprinting analyses. [B. J. Cargile, J. L. Stephenson, *Anal. Chem.* 2004, 76, 267-275. A. S. Essader, B. J. Cargile, J. L. Bundy, J. L. Stephenson, *Proteomics* 2005, 5, 24-34.]

To demonstrate that this invention and amphiphilic materials can selectively extract peptides with defined pI values from a proteolytic digest, a 1 μM solution of myoglobin was digested with trypsin, and the resulting peptide fragments were extracted at pH 7.1 using the same procedure described above. FIG. 3 shows typical MALDI mass spectra for the original myoglobin tryptic digest before extraction (3A) and the organic (3B) and aqueous (3C) phases after extraction with the inverse micelles in toluene. Table 2 summarizes the results of these experiments. All of the peptides with pI values above 7.1 are extracted effectively, and with only one exception, peptides with pI values below 7.1 are not extracted effectively. Among the peptide fragments tested, the only exception is the peptide N140-G153 (m/z 1553), a peptide fragment that has a pI below 7.1 and still has K>1. The calculated pI of this peptide is 6.9, and it exhibits an ion abundance ratio of 1.4. One of two reasons could explain the observed results: First, because the pH of the solution is so close to the pI of this peptide, a significant fraction of the peptide is positively-charged at pH 7.1 and therefore extracted. Alternatively, the theoretically calculated pI value may be low.

TABLE 2

Results obtained from the inverse micelle extraction of a myoglobin tryptic digest

| Sequence number | Amino acid sequence | SEQ ID NO | pI[a] | m/z | $(K \pm s_M)$[b] |
|---|---|---|---|---|---|
| 1-16 | GLSDGEWQQVLNVWGK | 1 | 4.1 | 1816 | 0.3 ± 0.1 |
| 17-31 | VEADIAGHGQEVLIR | 2 | 4.4 | 1606 | 0.3 ± 0.04 |
| 32-42 | LFTGHPETLEK (☐) | 3 | 5.3 | 1271 | 0.02 ± 0.02 |
| 32-47 | LFTGHPETLEKFDKFK | 4 | 7.8 | 1937 | 41 ± 6 |
| 57-77 | ASEDLKKHGTVVLTALGGILK | 5 | 9.8 | 2150 | 36 ± 4 |
| 63-78 | KHGTVVLTALGGILKK[c] | 6 | 10.9 | 1635 | — |
| 64-79 | HGTVVLTALGGILKKK[c] | 7 | 10.9 | 1635 | — |
| 63-77 | KHGTVVLTALGGILK | 8 | 10.6 | 1506 | 51 ± 10 |
| 64-78 | HGTVVLTALGGILKK | 9 | 10.6 | 1506 | 51 ± 10 |

TABLE 2-continued

Results obtained from the inverse micelle extraction of a myoglobin tryptic digest

| Sequence number | Amino acid sequence | SEQ ID NO | pI[a] | m/z | (K ± $s_M$)[b] |
|---|---|---|---|---|---|
| 64-77 | HGTVVLTALGGILK | 10 | 10.1 | 1378 | 32 ± 5 |
| 78-96 | KKGHHEAELKPLAQSHATK (●) | 11 | 10.2 | 2110 | 140 ± 12 |
| 79-96 | KGHHEAELKPLAQSHATK (■) | 12 | 9.8 | 1982 | 310 ± 0.2 |
| 80-96 | GHHEAELKPLAQSHATK | 13 | 8.0 | 1853 | 425 ± 61 |
| 103-118 | YLEFISDAIIHVLHSK | 14 | 6.0 | — | 0.0 |
| 119-133 | HPGDFGADAQGAMTK | 15 | 5.1 | 1502 | 0.05 ± 0.004 |
| 134-145 | ALELFRNDIAAK | 16 | 7.0 | 1360 | 0.7 ± 0.1 |
| 134-147 | ALELFRNDIAAKYK[c] | 17 | 9.6 | 1651 | — |
| 140-153 | NDIAAKYKELGFQG | 18 | 6.9 | 1553 | 1.4 ± 0.4 |
| 146-153 | YKELGFQG (o) | 19 | 6.4 | 942 | 0.01 ± 0.001 |

[a]Calculated in the same manner as Table 1.
[b]The ion abundance ratio is defined as the ratio of the MALDI ion abundance of the peptide in the organic phase that contains the inverse micelles ($I_{org}$) to the ion abundance of the peptide remaining in the aqueous phase ($I_{aq}$) (K = $I_{org}/I_{aq}$). Ion abundance ratio values (K) and standard errors of the mean ($s_M$) were for the [M + H]$^+$ signal of each peptide. In each case, the $s_M$ values are from 3 replicate measurements.
[c]Fragments observed only after extraction.

A closer look at some of the peptide fragments in Table 2 and FIG. 3 illustrates the success of the extraction process. For example, the peptides L32-K42 (□) and Y146-G153 (○) with pI values of 5.3 and 6.4, respectively, are negatively-charged at a solution pH of 7.1, and they are not significantly extracted into the organic phase; they remain in the aqueous phase after extraction. In contrast, the peptides K79-K96 (■) and K78-K96 (●) with pI values of 9.8 and 10.2, respectively, are positively charged, and they are efficiently extracted into the organic phase; very little of these peptides remains in the aqueous phase after extraction. Additionally, some peptide fragments that are not detected in the original tryptic digest can be observed in the organic phase after extraction. Isobaric fragments K63-K78 and K64-K79 and the peptide A134-K147 are examples of this situation. These peptides were not detected in the original digest, but after extraction they are readily observable. Each of these peptides has a pI value above the pH of the solution (see Table 2) and is consequently positively charged under the extraction conditions.

In addition to the selectivity shown above, the sensitivity of the extraction/detection technique is of interest. Indeed, a significant enhancement in peptide ion signals in the MALDI spectra after extraction using an inverse micelle polymer is observed. Assuming 100% extraction of the positively charged peptides from the aqueous solution, a 33-fold increase in peptide concentration is expected after extraction—due to the difference in volume of the aqueous and organic solutions in the extraction (1 mL aqueous solution vs. 30 μL organic solution). Surprisingly, peptide ion abundances from MALDI experiments are consistent with concentration factors of up to 400-fold in some cases.

Figure 10:
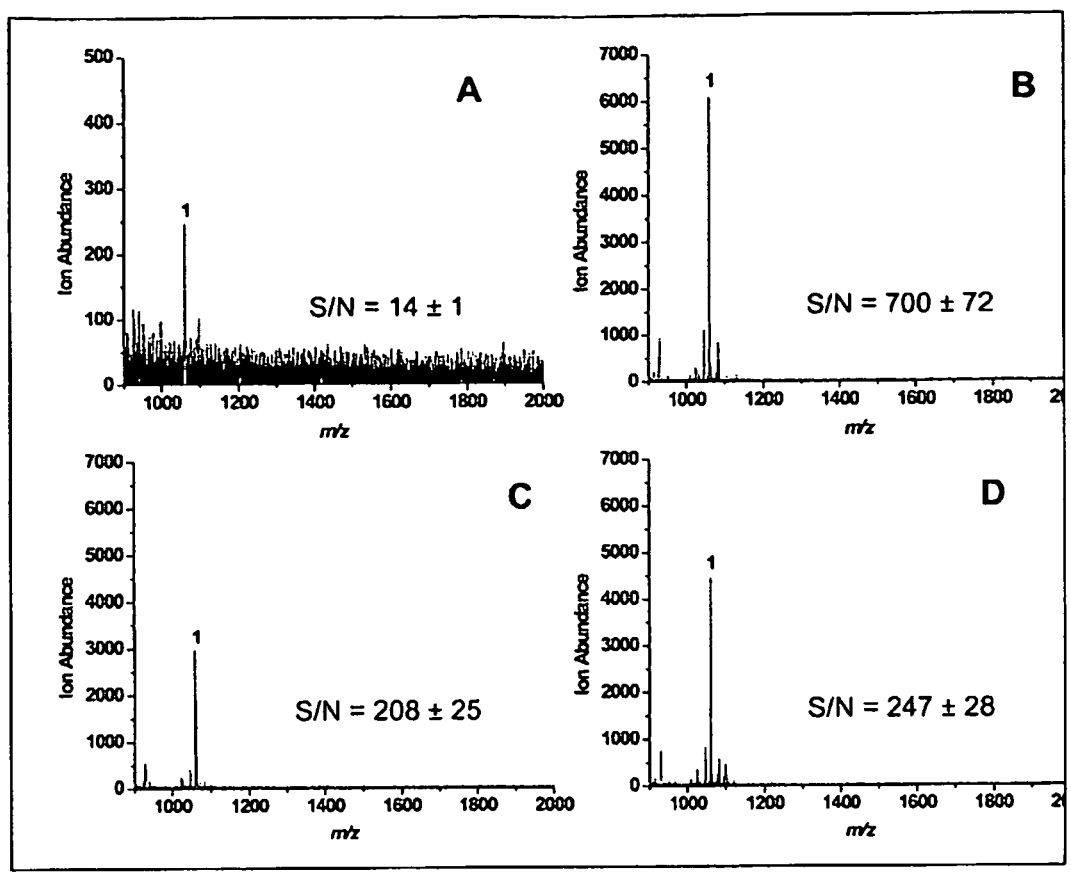
FIGS. 10A-D. A) MALDI mass spectrum of a 10 nM bradykinin solution; B) MALDI mass spectrum of 10 nM bradykinin after extraction using reverse micelles of polymer 1; C) MALDI mass spectrum of a 330 nM bradykinin solution; D) MALDI mass spectrum of 330 nM bradykinin solution using polymer 1 as additive to the matrix.
Figure 11:
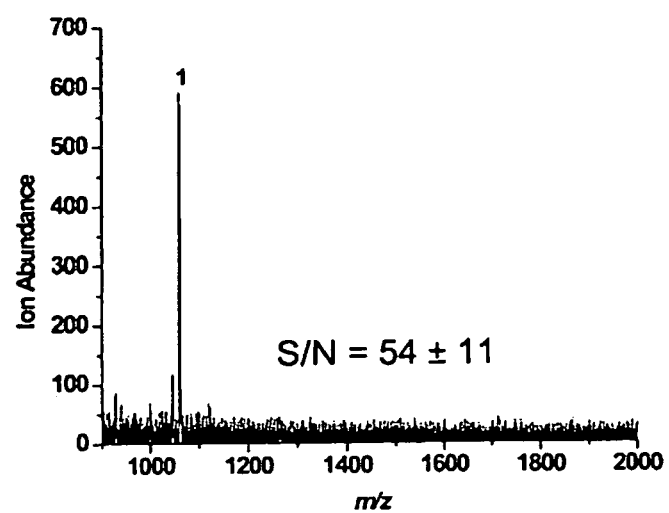
FIG. 11. MALDI mass spectrum of a 10 pM solution of bradykinin after extraction with the reverse micelles.

FIGS. 10A, 10B, and 10C illustrate this phenomenon by comparing a MALDI spectrum of a 10 nM solution of bradykinin before (10A) and after (10B) extraction with a MALDI mass spectrum of a 330 nM standard solution of the peptide (10C). Assuming that the peptide was completely extracted from the initial aqueous solution and considering the concentration factor, the ion abundance of the bradykinin ions in the organic extract (i.e. FIG. 10B) should be comparable to that of a 330 nM standard (i.e. FIG. 10C). Clearly ions abundances for bradykinin in spectra 10B and 10C are significantly different. Without limitation, two possible factors might explain this observation. First, upon spotting the extracted sample on the MALDI target, peptide-enriched zones are created. Second, the presence of the homopolymer during the MALDI process might be responsible for enhancement of the peptide's ion signal. Indeed, when peptide samples are mixed with the MALDI matrix containing 670 μM of homopolymer 1, a slight increase in peptide signal is observed (FIG. 10D), but this cannot account for the entire effect. Without limitation as to theory or mode of operation, it is possible that the polymer assists the matrix in coupling laser energy into peptide desorption/ionization because it exhibits residual absorption at 337 nm ($\epsilon$=1000 M$^{-1}$cm$^{-1}$), which is the laser wavelength in these MALDI experiments. Alternatively, without limitation, the peptide ion signals might also be enhanced by the presence of micellar assemblies in the MALDI matrix.

In view of the observed enhancement in ion signal after extraction with the inverse micelles, the detection limits of the procedure were tested. MALDI mass spectra with S/N ratios >50 can be reproducibly obtained from 10 pM solutions of peptides. For example, FIG. 5 shows the MALDI mass spectrum after extraction of bradykinin at this concentration. Without extraction, 10 pM solutions of bradykinin provide no observable MALDI signal for the peptide. If the expected concentration factor (i.e. 33-fold) is achieved during the extraction, then the amount of peptide on the MALDI target in this experiment is 330 amol. Indeed, the limit of detection for bradykinin without extraction is approximately 5 nM in the same MALDI equipment, which corresponds to 5 fmol on target under our experimental conditions.

Such representative embodiments demonstrate that: (i) the inverse micelles of this invention are capable of selectively extracting and concentrating peptides, where the selectivity depends on the pI; (ii) the pI cut-off for the selectivity in the extraction can be tuned by simply adjusting the pH of the solution; (iii) the pH-dependent cut-off can be utilized to further clean-up samples containing peptide mixtures; (iv) the technique can be used for selectively extracting and concentrating peptide fragments from a complex protein digest; (v) the increased sensitivity is not only due to a concentration effect but is also due to the fact that the polymeric material that is used provides an enhancement in MALDI ion yields; and (vi) the method(s) of this invention allow for detection of peptides from very dilute solutions. Accordingly, the amphiphilic polymers, inverse micelles thereof and related methods of this invention can be used to selectively concentrate proteolytic peptides with defined pIs. Further, the fact that the extracted peptides have a known range of pIs can be used as constraints during database searches for protein identification. In addition, by modifying the functionality of the polar group of the micelles, selectivity can be tuned for even more selective fractionation of complex mixtures, rendering such materials suitable for targeted protein extraction from cell lysates.

EXAMPLES OF THE INVENTION

The following non-limiting examples and data illustrate various aspects and features relating to the methods of the present invention, including the separation, extraction and/or mass spectrometric analysis of a protein or peptide mixture, as are available through the analytical methodologies described herein. In comparison with the prior art, the present methods provide results and data which are surprising, unexpected and contrary thereto. While the utility of this invention is illustrated through the separation, extraction and/or analysis of several protein/peptide mixtures and amphiphilic polymeric compounds and/or micelles which can be used therewith, it will be understood by those skilled in the art that comparable results are obtainable with various other separations, extractions/analyses and amphiphilic polymers/micelles, as are commensurate with the scope of this invention.

Reagents.

The fluorescent pI markers (Table 2), toluene and methanol were from Sigma-Aldrich (St. Louis, Mo.). Potassium phosphate and potassium hydrogen phthalate were acquired from Fisher scientific (Fair Lawn, N.J.). Potassium chloride, sodium borate and sodium chloride were obtained from Mallinckrodt (Paris, Ky.). Human bradykinin (MW 1060, RPPGFSPFR; SEQ ID NO:20), human kinetensin (MW 1172, IARRHPYFL; SEQ ID NO:21), human angiotensin I (MW 1296, DRVYIHPFHL; SEQ ID NO:22), human ACTH (1-13) (MW 1624, S YSMEHFRWGKPV; SEQ ID NO:23), bovine spinorphin (MW 877, LVVYPWT; SEQ ID NO:24), human β-amyloid(23-35) (MW 1404, EDVGSNKGAI-IGLM; SEQ ID NO:25) and human preproenkephalin (MW 1955, SSEVAGEGDGDSMGHEDLY; SEQ ID NO:26) were purchased from American Peptide Company (Sunnyvale, Calif.). Toluene, triflouroacetic acid (TFA), α-cyano-hydroxy cinnamic acid (α-CHCA), TRI S/TRI S-HCl and equine myoglobin were acquired from Sigma-Aldrich (St. Louis, Mo.). Trypsin was purchased from Promega (San Luis Obispo, Calif.). Tetrahydrofuran (THF) was obtained from Fisher Scientific (Pittsburgh, Pa.) and purified by distillation. All other chemicals were used as provided.

Instrumentation.

A Bruker Reflex III time-of-flight mass spectrometer was used to perform MALDI-MS analysis. The mass spectrometer is equipped with a 337-nm nitrogen laser, a 1.0 m flight tube, and a stainless steel sample target. All mass spectra were acquired in reflectron mode using a voltage of 16 kV. All reported spectra represent an average of 70 shots acquired at 30% laser power. The accelerating voltage was set to 20 kV.

Example 1

Polymer Synthesis and Aggregation

The procedure for synthesizing the homopolymers is described in the literature and in the aforementioned co-pending patent application. [Basu, S.; Vutukuri, D. R.; Shyamroy, S.; Sandanaraj, B. S.; Thayumanavan, S. *J. Am. Chem. Soc.* 2004, 126, 9890-9891.] Inverse micelles of 1 and 2 were prepared by dissolving an appropriate amount of the homopolymer (Mn~17,000 PDI=1.21) in toluene, for a final concentration of $1 \times 10^{-4}$ M, and adding 2 equivalents of water per equivalent of carboxylic acid (for 1) or pentaethyleneglycol group (for 2) to the organic phase. The equivalents of water are necessary to form a water pool inside the micelle and facilitate self-assembly. The mixture was sonicated until an optically clear solution was obtained.

Example 2a

Extraction Procedure

A typical biphasic extraction procedure involves mixing 200 μL of a toluene solution of homopolymer 1 or 2 ($1 \times 10^{-4}$ M) with 1 mL of an aqueous solution of peptide(s) that was buffered to pH ~7.0 with 50 mM Tris/TrisHCl. The mixture is vortexed for 10 to 120 minutes and centrifuged at 12000 rpm for 30-40 minutes to break the resulting emulsion and separate the organic and aqueous layers. The top (organic) layer is then recovered and dried to obtain a solid residue. The residue is redissolved into 10 μL of THF and sonicated for 10 seconds to promote solubilization. Finally, 20 μL of an α-CHCA matrix solution (0.16 Min 60:40:0.3% THF:H$_2$O:TFA) are added to the sample for a final volume of 30 μL. For MALDI-MS analysis the samples are applied to the target using the dried-droplet method, where 1 μL of the sample/matrix mixture is spotted on a stainless-steel target, and the solvent is evaporated at room temperature. The residual aqueous phase (~1 mL) after extraction is also examined by MALDI-MS. Equal amounts (5 μL) of the aqueous phase and the matrix solution (0.16 M α-CHCA in 60:40:0.3% THF:H$_2$O:TFA) are mixed, and 1 μL of the resulting solution is spotted, using the dried droplet method, on a stainless-steel target for MALDI-MS analysis.

Example 2b

For the sequential extraction experiments, 10 μL of the aqueous phase that is left after the first extraction were taken for MALDI analysis while the remaining 990 μL were acidified to the desired pH by adding dilute HCl. The acidified solution was then subjected to further extraction by adding another 200 μL of the homopolymer 1 ($1 \times 10^{-4}$ M in toluene) and repeating the same extraction procedure as described above.

Example 3

Polymer Synthesis and Reverse Micelle Formation

The monomer for the polymer was synthesized according to our previously reported procedure. The polymer was synthesized using reversible addition fragmentation chain transfer polymerization of the styrene based monomer that has t-butyl ester and n-decyl groups with ether linkages at meta positions relative to the olefinic group. 2-cyanoisopropyl dithiobenzoate was used as the chain transfer agent, and t-butyl ester was hydrolyzed after polymerization. (See, S. Basu, D. R. Vutukuri and S. Thayumanavan, *J. Am. Chem. Soc.* 2005, 127, 16794-16795; E. N. Savariar, S. V. Aathimanikandan and S. Thayumanavan, *J. Am. Chem. Soc.* 2006, 128, 16224-16230.) The number average molecular weight ($M_n$) of the polymer, which was determined using size exclusion chromatography (SEC) before ester hydrolysis, was found to be 25 kDa with a polydispersity index (PDI) of 1.32.

The polymeric reverse micelle solution of the polymer was prepared according to the literature; Basu et al., infra. In this experiment, 10 mg of the polymer was dissolved in toluene to obtain a concentration of $1 \times 10^{-4}$ M, and 2 equivalents of water per monomer were added to the toluene to generate the water pool in the reverse micelle interiors. The solution was sonicated for 6 hrs or until a visibly clear solution was obtained. This solution was then used for the liquid-liquid extraction.

Example 4

Liquid-Liquid Extraction Procedure

A two-phase liquid-liquid extraction protocol that was previously developed was employed. (See, M. Y. Combariza, E. N. Savariar, D. R. Vutukuri, S. Thayumanavan and R. W. Vachet, *Anal. Chem.* 2007, 79, 7124-7130.) An aqueous solution of each pI marker was prepared at a given pH between 1.5 and 11.5 using an appropriate buffer. The extraction was performed by first mixing a toluene solution (100 μL) of the polymeric inverse micelles ($1 \times 10^{-4}$ M of polymer) with an aqueous solution (500 μL) of a given pI marker ($1 \times 10^{-6}$ M), buffered to the desired pH. The mixture was then vortexed for 120 minutes. After mixing, the sample was centrifuged at 12000 rpm for 45 minutes to break the resulting emulsion. The top (organic) layer was removed and the bottom (aqueous) layer was analyzed by fluorescence spectroscopy. Three replicate extractions by the polymeric reverse micelles were carried out for each marker at each pH value.

Example 5

Fluorescence Measurements

The amount of pI marker left in the bottom (aqueous) layer after extraction was determined on a Photon Technology International fluorometer (Ontario, Canada). Analysis of the organic phase was difficult because the fluorescence spectrum of the polymer in this phase was very broad, and in many cases overlapped with the signal from the pI markers. The excitation and emission wavelengths for each pI marker were chosen to maximize the fluorescence signal. Standard solutions with concentrations ranging from $1 \times 10^{-8}$ to $5 \times 10^{-6}$ M were prepared for each marker at each different pH value to construct calibration curves. For most of the pI markers, the fluorescence intensity was very low under more acidic conditions, making it difficult to collect data at these lower pHs. The fluorescence intensity of the aqueous phase after a given extraction was measured, and in each case the fluorescence intensity was used to determine the concentration of the pI marker remaining in the aqueous phase after the extraction. The amount of pI marker that was extracted by the reverse micelles was then calculated by subtracting the remaining aqueous phase concentration from the initial concentration ($1 \times 10^{-6}$ M). The fluorescence measurements were repeated at least 3 times for each extracted sample and the average values are reported.

Example 6

Theoretical Calculations

To better understand the extraction behavior of the pI markers, theoretical calculations of the species present in solution at the different aqueous pH were performed. All of the pI markers studied (Table 1) are diprotic systems, and therefore simple equations can be used to calculate the fractional composition of each species in the aqueous solutions. The chemical equilibrium of diprotic compounds ($H_2A$) are:

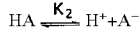

$K_1$: acid dissociation constant of $H_2A^+$
$K_2$: acid dissociation constant of HA For a diprotic system, designate the fraction in the form $H_2A^+$ as $\alpha_{H2A^+}$, the fraction in the form HA as $\alpha_{HA}$, and the fraction in the form $A^-$ as $\alpha_{A^-}$. Equations (1)-(4) are used to calculate these fractional compositions.

$$\alpha_{H_2A^+} = \frac{[H_2A^+]}{F} = \frac{[H^+]^2}{[H^+]^2 + [H^+K_1] + K_1K_2} \quad (1)$$

$$\alpha_{HA} = \frac{[HA]}{F} = \frac{K_1[H^+]}{[H^+]^2 + [H^+]K_1 + K_1K_2} \quad (2)$$

$$\alpha_{A^-} = \frac{K_1K_2}{[H^+]^2 + [H^+]K_1 + K_1K_2} \quad (3)$$

$$\alpha_{H2A}^+ + \alpha_{HA} + \alpha_A^- = 1 \quad (4)$$

In this study, the calculated fractional compositions were converted to percentage fractional composition in order to compare with the percentage extractions obtained from the experimental results.

Example 7

Extraction of the myoglobin digest was done in a manner similar to described above. 1 mL aliquots of a $1 \times 10^{-6}$ M protein digest were buffered at pH 7.1 with 50 mM TRIS, mixed with 200 μL of a toluene solution of homopolymer 1 ($1 \times 10^{-4}$ M), extracted, and analyzed by MALDI-MS as detailed above.

Example 8

Proteolytic digestion. For the myoglobin tryptic digests, 110 μl of protein solution ($\sim 3 \times 10^{-4}$ M in 50 mM TRIS buffer) were mixed with 40 μL of MeOH. The mixture was heated at 60° C. for 10 minutes to denature the protein. 150 μL of a trypsin solution, which contained 2 μg/450 μL of protein, 50 mM TRIS buffer, and 1 mM $CaCl_2$, was added to the denatured protein sample, and the mixture was left to digest at 37° C. for 24 hours. The digestion was stopped by filtering the solution through a 10K MWCO Centricon filter. The filtrates were diluted to the desired concentration and used for extraction and analysis.

Example 9

Extraction of peptide mixture by positively charged polymer. Illustrating other embodiments of this invention, positively-charged polymers extract peptides with pI values below the aqueous solution pH. Without limitation, polymers with moieties comprising a positively charged nitrogenous group can be used with good effect. Representative of such embodiments, an imidazole-substituted polymer, 4, shown below, can be prepared using straight forward synthetic techniques of the sort described herein, and/or as are well-known to those skilled in the art. Selective extraction was demonstrated using the peptide mixture of Table 3.

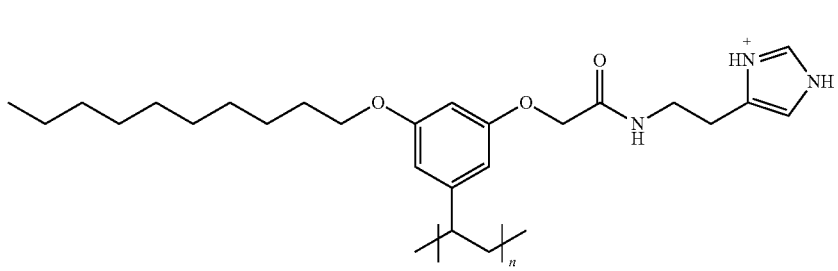

4

| Peptide | pI | Sequence | m/z | Peak no. in mass spectrum |
|---|---|---|---|---|
| Kinetensin | 11.1 | IARRHPYFL | 1172 | 2 |
| Angiotensin | 7.7 | DRVYIHPFHL | 1296 | 4 |
| Preproenkephalin | 3.6 | SSEVAGEGDGDSMGHEDLY | 1955 | 7 |

TABLE 3

Figure 12A:
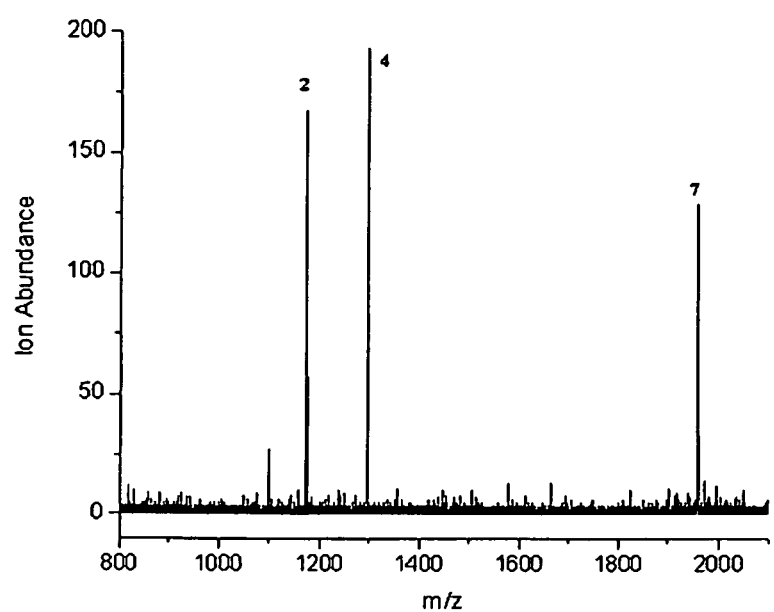
FIGS. 12A-C. Mass spectra of a peptide mixture before (A) and after (B, organic phase; and C, aqueous phase) extraction, in accordance with an embodiment of this invention.
Figure 12B:
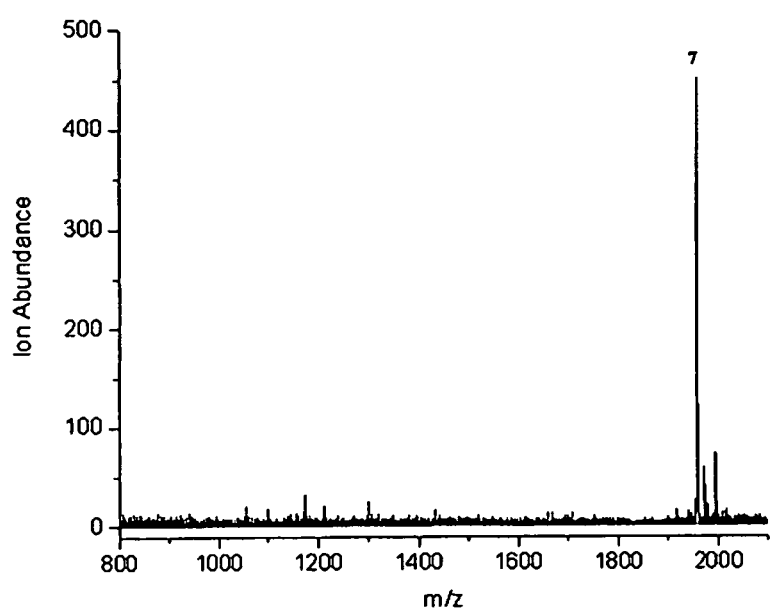
Figure 12C:
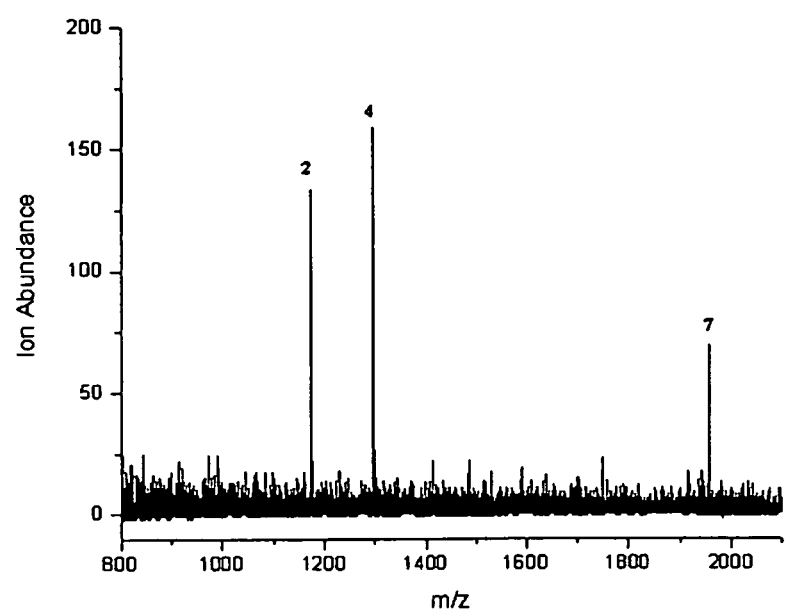

FIG. 12A shows the mass spectrum of the peptide mixture before extraction (concentration of each peptide is $1.0 \times 10^{-6}$ M). FIG. 12B shows the mass spectrum of the organic phase after extraction at pH 4.5. At pH 4.5, kinetensin and angiotensin are positively-charged because the pH is below their pI values. Preproenkephalin (7) is negatively charged because the pH is above its pI value. FIG. 12C provides a mass spectrum of the aqueous phase after extraction at pH 4.5. The positively-charged peptides remain in the aqueous phase after extraction. Without limitation, a small percentage of the preproenkephalin is believed to remain in the aqueous phase because a small percentage of this peptide is neutral at pH 4.5

We claim:

1. A method of using an amphiphilic polymeric micelle for selective analyte extraction, such method comprising:
   providing a buffered aqueous medium comprising a plurality of analyte components, said medium comprising a pH selected from lower than and higher than the isoelectric point of at least one said analyte component; and
   contacting said buffered aqueous medium with another medium at least partially immiscible with said buffered aqueous medium, said other medium comprising an amphiphilic polymeric compound comprising a reverse micellar configuration in said other medium and a moiety capable of interactive association with at least one said analyte component at said pH.

2. The method of claim 1 wherein said amphiphilic polymer compound is of a formula

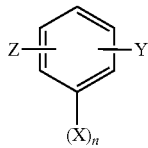

wherein X is selected from alkylene and substituted alkylene moieties, and n is an integer greater than about 20; Y is selected from alkyl, substituted alkyl, alkoxy, substituted alkoxy and poly(ethylene oxide) moieties; and Z is selected from alkylamidoalkylimidazole, alkylamidoalkylimidazolium salt, oxasubstituted alkylamidoalkylimidazole and oxasubstituted alkylamidoalkylimidazolium salt, carboxylic acid, alkyl carboxylic acid, alkyl carboxylic acid salt, oxasubstituted alkylcarboxylic acid and oxasubstituted alkylcarboxylic acid salt moieties.

3. The method of claim 2 wherein said moiety comprises a carboxylate group.

4. The method of claim 1 wherein said pH is adjusted to a value selected from lower than and higher than the isoelectric point for another said analyte component, for sequential extraction.

5. The method of claim 1 wherein at least one said analyte component is a peptide.

6. The method of claim 5 wherein said peptide component is in an amount less than sufficient to provide a MALDI signal under mass spectroscopic analysis.

7. The method of claim 5 wherein at least one said peptide component is concentrated.

8. The method of claim 7 wherein said peptide component is applied to a target component of a mass spectrometer.

9. A method of sequential fractionation of a peptide mixture, said method comprising:
   providing a buffered aqueous medium comprising a mixture of peptide components, said medium comprising a pH selected from lower than and higher than the isoelectric point of at least one said peptide fraction of said mixture;
   contacting said buffered aqueous medium with another medium at least partially immiscible with said buffered aqueous medium, said other medium comprising an amphiphilic polymeric compound comprising a reverse micellar configuration in said other medium and a moiety capable of electrostatic interaction with at least one said peptide fraction to separate said isoelectric peptide fraction;
   adjusting the pH of said buffered aqueous medium, said adjusted pH below the isoelectric point of at least another said peptide fraction; and
   contacting said pH-adjusted buffered aqueous medium with said other medium, to separate said other isoelectric peptide fraction.

10. The method of claim 9 comprising an amphiphilic polymer compound of a formula

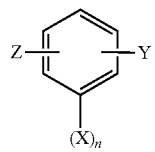

wherein X is selected from alkylene and substituted alkylene moieties, and n is an integer greater than about 20; Y is selected from alkyl, substituted alkyl, alkoxy, substituted alkoxy and poly(ethylene oxide) moieties; and Z is selected from alkylamidoalkylimidazole, alkylamidoalkylimidazolium salt, oxasubstituted alkylamidoalkylimidazole and oxasubstituted alkylamidoalkylimidazolium salt, carboxylic acid, alkylcarboxylic acid, alkylcarboxylic acid salt, oxasubstituted alkylcarboxylic acid and oxasubstituted alkylcarboxylic acid salt moieties.

11. The method of claim 9 comprising iterative pH adjustments and peptide contact, to sequentially separate peptide fractions from said mixture.

12. The method of claim 9 wherein said mixture can be selected from multi-protein digests, cell lysates and tissue extracts.

13. The method of claim 9 wherein each said separated fraction is analyzed by mass spectrometry.

14. The method of claim 13 wherein the isoelectric point of each said separated fraction and a m/z ratio obtained are used to identify the peptide source of a said fraction.

15. A method of MALDI mass spectrometric analysis of an analyte mixture, said mixture comprising:
    providing a buffered aqueous medium comprising a plurality of analyte components, said medium comprising a pH selected from lower than and higher than the isoelectric point of at least one analyte component;
    contacting said buffered aqueous medium with another medium at least partially immiscible with said buffered aqueous medium, said other medium comprising an amphiphilic polymeric compound comprising a reverse micellar configuration in said other medium and a moiety capable of interactive association with at least one said analyte component at said pH, to separate a said isoelectric analyte component from said buffered aqueous medium;
    applying said separated analyte component to a mass spectrometric target; and
    acquiring a MALDI-mass spectrum of a said separated analyte component, said spectrum comprising analyte ion signals for each said separated analyte component.

16. The method of claim 15 wherein at least one said analyte component is a peptide.

17. The method of claim 15 wherein a MALDI-mass spectrum of a said buffered aqueous medium is absent a peptide ion signal prior to separation therefrom.

18. The method of claim 16 wherein said peptide component has a concentration less than about 5 nM, and a MALDI-mass spectrum of said buffered aqueous medium is absent observable peptide signals.

19. The method of claim 18 wherein said separated peptide component spectrum is observable at a concentration less than about 5 nM.

20. The method of claim 15 wherein said amphiphilic polymer compound is of a formula

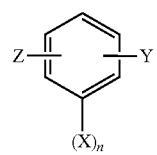

wherein X is selected from alkylene and substituted alkylene moieties, and n is an integer greater than about 20; Y is selected from alkyl, substituted alkyl, alkoxy, substituted alkoxy and poly(ethylene oxide) moieties; and Z is selected from alkylamidoalkylimidazole, alkylamidoalkylimidazolium salt, oxasubstituted alkylamidoalkylimidazole and oxasubstituted alkylamidoalkylimidazolium salt, carboxylic acid, alkylcarboxylic acid, alkylcarboxylic acid salt, oxasubstituted alkylcarboxylic acid and oxasubstituted alkylcarboxylic acid salt moieties.

* * * * *

SEQUENCE LISTING

```
<160> NUMBER OF SEQ ID NOS: 26

<210> SEQ ID NO 1
<211> LENGTH: 16
<212> TYPE: PRT
<213> ORGANISM: Equus caballus

<400> SEQUENCE: 1

Gly Leu Ser Asp Gly Glu Trp Gln Gln Val Leu Asn Val Trp Gly Lys
1               5                   10                  15

<210> SEQ ID NO 2
<211> LENGTH: 15
<212> TYPE: PRT
<213> ORGANISM: Equus caballus

<400> SEQUENCE: 2

Val Glu Ala Asp Ile Ala Gly His Gly Gln Glu Val Leu Ile Arg
1               5                   10                  15

<210> SEQ ID NO 3
<211> LENGTH: 11
<212> TYPE: PRT
<213> ORGANISM: Equus caballus

<400> SEQUENCE: 3

Leu Phe Thr Gly His Pro Glu Thr Leu Glu Lys
1               5                   10

<210> SEQ ID NO 4
<211> LENGTH: 16
<212> TYPE: PRT
<213> ORGANISM: Equus caballus

<400> SEQUENCE: 4

Leu Phe Thr Gly His Pro Glu Thr Leu Glu Lys Phe Asp Lys Phe Lys
1               5                   10                  15
```

```
<210> SEQ ID NO 5
<211> LENGTH: 21
<212> TYPE: PRT
<213> ORGANISM: Equus caballus

<400> SEQUENCE: 5

Ala Ser Glu Asp Leu Lys Lys His Gly Thr Val Val Leu Thr Ala Leu
1               5                   10                  15

Gly Gly Ile Leu Lys
            20

<210> SEQ ID NO 6
<211> LENGTH: 16
<212> TYPE: PRT
<213> ORGANISM: Equus caballus

<400> SEQUENCE: 6

Lys His Gly Thr Val Val Leu Thr Ala Leu Gly Gly Ile Leu Lys Lys
1               5                   10                  15

<210> SEQ ID NO 7
<211> LENGTH: 16
<212> TYPE: PRT
<213> ORGANISM: Equus caballus

<400> SEQUENCE: 7

His Gly Thr Val Val Leu Thr Ala Leu Gly Gly Ile Leu Lys Lys Lys
1               5                   10                  15

<210> SEQ ID NO 8
<211> LENGTH: 15
<212> TYPE: PRT
<213> ORGANISM: Equus caballus

<400> SEQUENCE: 8

Lys His Gly Thr Val Val Leu Thr Ala Leu Gly Gly Ile Leu Lys
1               5                   10                  15

<210> SEQ ID NO 9
<211> LENGTH: 15
<212> TYPE: PRT
<213> ORGANISM: Equus caballus

<400> SEQUENCE: 9

His Gly Thr Val Val Leu Thr Ala Leu Gly Gly Ile Leu Lys Lys
1               5                   10                  15

<210> SEQ ID NO 10
<211> LENGTH: 14
<212> TYPE: PRT
<213> ORGANISM: Equus caballus

<400> SEQUENCE: 10

His Gly Thr Val Val Leu Thr Ala Leu Gly Gly Ile Leu Lys
1               5                   10

<210> SEQ ID NO 11
<211> LENGTH: 19
<212> TYPE: PRT
<213> ORGANISM: Equus caballus
```

<400> SEQUENCE: 11

Lys Lys Gly His His Glu Ala Glu Leu Lys Pro Leu Ala Gln Ser His
1               5                   10                  15

Ala Thr Lys

<210> SEQ ID NO 12
<211> LENGTH: 18
<212> TYPE: PRT
<213> ORGANISM: Equus caballus

<400> SEQUENCE: 12

Lys Gly His His Glu Ala Glu Leu Lys Pro Leu Ala Gln Ser His Ala
1               5                   10                  15

Thr Lys

<210> SEQ ID NO 13
<211> LENGTH: 17
<212> TYPE: PRT
<213> ORGANISM: Equus caballus

<400> SEQUENCE: 13

Gly His His Glu Ala Glu Leu Lys Pro Leu Ala Gln Ser His Ala Thr
1               5                   10                  15

Lys

<210> SEQ ID NO 14
<211> LENGTH: 16
<212> TYPE: PRT
<213> ORGANISM: Equus caballus

<400> SEQUENCE: 14

Tyr Leu Glu Phe Ile Ser Asp Ala Ile Ile His Val Leu His Ser Lys
1               5                   10                  15

<210> SEQ ID NO 15
<211> LENGTH: 15
<212> TYPE: PRT
<213> ORGANISM: Equus caballus

<400> SEQUENCE: 15

His Pro Gly Asp Phe Gly Ala Asp Ala Gln Gly Ala Met Thr Lys
1               5                   10                  15

<210> SEQ ID NO 16
<211> LENGTH: 12
<212> TYPE: PRT
<213> ORGANISM: Equus caballus

<400> SEQUENCE: 16

Ala Leu Glu Leu Phe Arg Asn Asp Leu Ala Ala Lys
1               5                   10

<210> SEQ ID NO 17
<211> LENGTH: 14
<212> TYPE: PRT
<213> ORGANISM: Equus caballus

<400> SEQUENCE: 17

Ala Leu Glu Leu Phe Arg Asn Asp Leu Ala Ala Lys Tyr Lys
1               5                   10

```
<210> SEQ ID NO 18
<211> LENGTH: 14
<212> TYPE: PRT
<213> ORGANISM: Equus caballus

<400> SEQUENCE: 18

Asn Asp Leu Ala Ala Lys Tyr Lys Glu Leu Gly Phe Gln Gly
1               5                   10

<210> SEQ ID NO 19
<211> LENGTH: 8
<212> TYPE: PRT
<213> ORGANISM: Equus caballus

<400> SEQUENCE: 19

Tyr Lys Glu Leu Gly Phe Gln Gly
1               5

<210> SEQ ID NO 20
<211> LENGTH: 9
<212> TYPE: PRT
<213> ORGANISM: Homo sapiens

<400> SEQUENCE: 20

Arg Pro Pro Gly Phe Ser Pro Phe Arg
1               5

<210> SEQ ID NO 21
<211> LENGTH: 9
<212> TYPE: PRT
<213> ORGANISM: Homo sapiens

<400> SEQUENCE: 21

Ile Ala Arg Arg His Pro Tyr Phe Leu
1               5

<210> SEQ ID NO 22
<211> LENGTH: 10
<212> TYPE: PRT
<213> ORGANISM: Homo sapiens

<400> SEQUENCE: 22

Asp Arg Val Tyr Ile His Pro Phe His Leu
1               5                   10

<210> SEQ ID NO 23
<211> LENGTH: 13
<212> TYPE: PRT
<213> ORGANISM: Homo sapiens

<400> SEQUENCE: 23

Ser Tyr Ser Met Glu His Phe Arg Trp Gly Lys Pro Val
1               5                   10

<210> SEQ ID NO 24
<211> LENGTH: 7
<212> TYPE: PRT
<213> ORGANISM: Bos taurus

<400> SEQUENCE: 24

Leu Val Val Tyr Pro Trp Thr
1               5
```

```
<210> SEQ ID NO 25
<211> LENGTH: 14
<212> TYPE: PRT
<213> ORGANISM: Homo sapiens

<400> SEQUENCE: 25

Glu Asp Val Gly Ser Asn Lys Gly Ala Ile Ile Gly Leu Met
1               5                  10

<210> SEQ ID NO 26
<211> LENGTH: 19
<212> TYPE: PRT
<213> ORGANISM: Homo sapiens

<400> SEQUENCE: 26

Ser Ser Glu Val Ala Gly Glu Gly Asp Gly Asp Ser Met Gly His Glu
1               5                  10                  15

Asp Leu Tyr
```